United States Patent [19]

Dockner et al.

[11] Patent Number: 4,943,671
[45] Date of Patent: Jul. 24, 1990

[54] REDUCTIVE DEHALOGENATION OF ORGANIC HALOGEN COMPOUNDS

[75] Inventors: Toni Dockner, Meckenheim; Manfred Sauerwald, Roedersheim-Gronau; Herbert Krug, Ludwigshafen; Matthias Irgang, Heidelberg, all of Fed. Rep. of Germany

[73] Assignee: BASF Aktiengesellschaft, Ludwigshafen, Fed. Rep. of Germany

[21] Appl. No.: 189,362

[22] Filed: May 2, 1988

[30] Foreign Application Priority Data

May 12, 1987 [DE] Fed. Rep. of Germany ....... 3715751

[51] Int. Cl.$^5$ ............................ C07C 1/00; C07C 1/30
[52] U.S. Cl. ..................................... 585/642; 585/469; 585/641; 585/809; 570/227; 570/230; 502/185; 423/481; 208/262.1; 546/152; 546/250; 548/335; 548/400
[58] Field of Search ................ 570/230, 227; 585/641, 585/642, 469, 809; 502/185; 208/262.1; 423/481

[56] References Cited

U.S. PATENT DOCUMENTS 3,006,727 10/1961 Ruh et al. ............................ 585/641
4,824,956 4/1989 Dockner et al. ..................... 546/314

FOREIGN PATENT DOCUMENTS 3510033 9/1986 Fed. Rep. of Germany .
3510034 9/1986 Fed. Rep. of Germany .
235630 5/1986 German Democratic Rep. .................... 585/642

OTHER PUBLICATIONS

Chem. Abstracts (105) 208450r, 1986, Marschner [Abstract of E. Griman Pat. DD 235630 pub. 5/14/86].

*Primary Examiner*—Anton H. Sutto
*Assistant Examiner*—Philip Datlow
*Attorney, Agent, or Firm*—John H. Shurtleff

[57] ABSTRACT

Organic halogen compounds in which one or more halogen atoms are covalently bonded to the carbon are subjected to reductive dehalogenation by reaction with a hydrocarbon in the presence of carbon at elevated temperatures with formation of a hydrogen halide, by a process in which the dehalogenation is carried out in the presence of iron powder or an iron compound as a cocatalyst, at from 100° to 450° C.

14 Claims, No Drawings

REDUCTIVE DEHALOGENATION OF ORGANIC HALOGEN COMPOUNDS

The present invention relates to an improved process for the reductive dehalogenation of organic halogen compounds in which one or more halogen atoms are covalently bonded to the carbon, by reaction with a hydrocarbon in the presence of carbon at elevated temperatures with formation of a hydrogen halide.

German Laid-Open Applications DOS No. 3,510,033 and 3,510,034 describe a widely applicable process, which is easy to carry out industrially, for the reductive dehalogenation of organic halogen compounds with formation of hydrocarbons and hydrogen halides. In this process, aliphatic, cycloaliphatic, aromatic or aliphatic halogen compounds are reacted in the liquid phase of from 100° to 450° C. or in the gas phase at from 200° to 600° C. with a hydrocarbon in the presence of carbon. Examples of hydrocarbons used in reactions in the liquid phase are high boiling mineral oil fractions, such as vacuum residues, heavy fuel oil or industrial white oil, and examples of those used in reactions in the gas phase are cheap, low boiling aliphatic hydrocarbons, such as isobutane.

The disadvantage of these processes is the fact that the hydrogen content of the hydrocarbons is not yet adequately utilized for the reductive dehalogenation (cf. Comparative Examples).

East German Patent No. 235,630 discloses a process in which 1,2-dichloropropane is cleaved to give propene and chloropropene, without the addition of hydrocarbons, in the gas phase at from 170° to 450° C. over active carbon which has been treated with a suspension of iron oxides and/or iron oxide hydroxides and then dried at from 80° to 200° C. No amounts are stated in connection with the gaseous reaction mixture, but it consists of only 75.2% by volume of propene, the remainder being cis/trans-1-chloropropene.

It is an object of the present invention to provide a dehalogenation process which is distinguished by high conversions, high selectivity and better utilization of the added hydrocarbon.

We have found that this object is achieved by a process for the reductive dehalogenation of organic halogen compounds in which one or more halogen atoms are covalently bonded to the carbon, by reaction with a hydrocarbon in the presence of carbon at elevated temperatures with formation of a hydrogen halide, wherein the dehalogenation is carried out in the presence of an iron compound as cocatalyst at from 100° to 450° C.

The hydrogen required for the formation of hydrogen halide is derived from the hydrocarbon, from which, in addition to derivatives having a lower hydrogen content, predominantly carbon is formed.

High boiling mineral oils whose boiling points are higher than the reaction temperature, which is from 100° to 450° C., preferably from 200° to 400° C., in particular from 250° to 350° C., can advantageously be used as hydrocarbons. Examples of such hydrocarbons are vacuum gas oil, industrial white oil, fuel oil, heavy fuel oil, vacuum residues and other high boiling components obtained in the fractionation of mineral oil.

Moreover, it is also possible to use lower boiling hydrocarbons, such as methane, ethane, acetylene, propane, propene, butane, butene, pentane, pentene, cyclopentane, hexane, hexene, cyclohexane or 1,2,3,4-tetrahydronaphthalene, or lower boiling hydrocarbon mixtures, e.g. light fuel oil, gasoline, naphtha or liquefied petroleum gas.

The ratios of hydrocarbon to halogen compound are as a rule from 0.2 to 5, in particular from 0.5 to 3.

The dehalogenation reaction can be carried out under atmospheric, superatmospheric or reduced pressure. While atmospheric pressure is generally most advantageous when high boiling hydrocarbons are used, the reaction is most advantageously carried out in the gas phase or under superatmospheric pressure in the liquid phase when lower boiling hydrocarbons are employed.

In the reaction in the liquid phase, which is generally preferred, the major part or all of the reacting hydrocarbons should be in liquid form. The liquid phase contains suspended carbon, which is formed during the reaction, is added or is present as a component of the hydrocarbons. By adding elemental carbon to the reaction mixture, the reaction is accelerated and the conversion increased, particularly if the hydrocarbon contains little or no carbon. The reaction mixture preferably contains from 1 to 50, in particular from 5 to 20, % by weight of carbon. Examples of suitable carbon additives are oil coke and carbon black or another form of graphite; active carbons, such as Carboraffin P ® animal carbon which has been activated with, for example, $ZnCl_2$, phosphoric acid or hydrogen, are particularly advantageously used.

According to the invention, the dehalogenation is carried out in the presence of carbon and additionally in the presence of an iron compound as cocatalyst. Suitable iron compounds are divalent and/or trivalent compounds of iron, for example iron halides, such as chlorides or bromides, iron sulfate, iron nitrate, iron phosphate, iron thiocyanate, iron chromate, iron(II) oxalate, iron(III) acetate, iron(III) formate and in particular iron oxides, iron oxide hydroxides or iron sulfides. The following compounds may be mentioned as examples: iron(II) oxide, iron(III) oxide ($\alpha$- or $\gamma$-modification), iron(II,III) oxide, iron oxide hydroxide, such as geothite or lepidocrocite, iron(II) sulfide, iron(II) disulfide (pyrites) or iron(III) sulfide. It is also possible to use mixtures of the stated compounds or elemental iron. Iron(II) sulfide and disulfide and especially $Fe_2O_3$ are particularly preferred.

By adding these iron compounds as a cocatalyst in addition to carbon, the amount of hydrocarbon previously required for hydrogen transfer can be dramatically reduced. Moreover, the dehalogenation reaction can then be carried out at lower temperatures with high conversions.

The amount of the iron cocatalyst in the reaction mixture is in general about 0.001–10, in particular 0.5–5, % by weight, based on hydrocarbon/carbon. Larger amounts are possible but as a rule are not necessary. The iron compound can be added to the reaction mixture, but it is also possible for carbon powder or moldings to be impregnated beforehand with the iron compounds and, if desired, to be calcined, and the active carbon catalysts laden with the iron compounds then to be used, this being particularly appropriate in reactions in the gas phase.

The gas-phase dehalogenation can be carried out by the fixed-bed or fluidized bed method, the carbon being used in the form of pellets or extrudates or as fluidizable catalyst, for example having carbon particles smaller than 1 mm in diameter. It is also possible to produce the active carbon in the reaction mixture by carrying out the reaction in the presence of a surface-active solid phase, with the result that catalytically active carbon is deposited on the said solid phase from the beginning of the reaction onward.

Surface-active minerals, such as silica gel, alumina, etc., are advantageously used as the solid phase. Other suitable examples are the oxides of the elements of main groups II, III, IV and/or V of the Periodic Table and of subgroup IV, such as MgO, MgSiO$_3$, CaO, B$_2$O$_3$ and TiO$_2$, in particular oxides of silicon or aluminum.

Compounds used as organic halogen compounds are those in which one or more halogen atoms, such as iodine, bromine or chlorine, are covalently bonded to the carbon. These starting materials may be aliphatic, cycloaliphatic, aromatic or araliphatic halogen compounds, as described in, for example, German Laid-Open Applications DOS Nos. 3,510,033 or 3,510,034.

Examples of suitable compounds are straight-chain, branched or cyclic monohaloalkanes, such as chloroethane, 1-chloro-2-phenylethane, 1-chloropropane, 1-chloro-2-methylpropane, 2-bromopropane, 1-iodobutane, 1-chloropentane, tert-butyl iodide, chlorocyclohexane or chlorocyclopentane.

Furthermore, olefinically unsaturated monohalogen compounds can be dehalogenated to give alkenes, examples being allyl chloride, 1-bromobut-1-ene, 2-bromobut-2-ene, 1-iodopent-2-ene, 1-chlorocyclohex-1-ene, 1-bromocyclohex-2-ene, cinnamyl chloride and β-bromostyrene.

Particularly suitable starting materials are vicinal dihalides of the general formula I

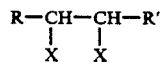

where X is iodine, bromine and/or chlorine and R and R' independently of one another are each hydrogen, an aliphatic radical, for example alkyl of 1 to 20, in particular 1 to 5, carbon atoms, cycloalkyl, for example cycloalkyl of 5 to 8 carbon atoms, aryl or aralkyl, in particular of 6 to 12 carbon atoms, or both radicals, together with the carbon atoms to which they are bonded, form a cycloalkane of 4 to 12, in particular 4 to 8, carbon atoms. Polyhalogen compounds can also advantageously be reacted.

Examples of suitable compounds are 1,2-dichloropropane, 1,2-dichlorobutane, 1,2-dichloropentane, 1,2-dibromobutane, 2,3-diiodobutane, 1,2-dibromo-,2-methylpropane, 1,2-dibromocyclobutane, 1,2-dibromocyclohexane, 1,2-dichloro-1,2-diphenylethane, 1,2-dichloro-3-phenylpropane, 1-bromo-2-iodobutane and 1-bromo-2-chloroethane, as well as 1,1,2-trichloroethane and hexachlorocyclohexane (HCH).

The starting compounds described are not intended to restrict the range of application of the novel process. The halogen compounds may additionally carry substituents which are inert under the reaction conditions, such as cyano, alkoxy, dialkylamino, phenyl or substituted phenyl groups. Heterocyclic compounds, for example halogen-substituted pyridine, quinoline, pyrrole or imidazole, can also be reacted.

Depending on the reaction temperature, the dehalogenation of hexachlorocyclohexane leads to 1,3,5-trichloro-, m-dichloro- and monochlorobenzene and finally benzene.

Examples of aromatic halogen compounds which are reacted are halobenzenes, such as bromobenzene, metadichorobenzene or 1,3,5-trichlorobenzene, halotoluenes, such as p-bromotoluene or 2,4-dichlorotoluene, halogenated biphenyls or triphenyls, such as diphenyl or triphenyl chlorides or polychlorobiphenyl (PCB), and halogenated naphthalenes, such as chloro- or bromonaphthalene or penta- or hexachloronaphthalene.

The aromatically bonded halogen atoms are substituted by hydrogen. Polyhalogenated aromatics are reductively dehalogenated stepwise to the halogen-free hydrocarbon. Thus, reaction of polychlorobiphenyl with vacuum residue gives hydrogen chloride and diphenyl.

The novel process can be very advantageously used to reduce aromatic or heteroaromatic acyl halides, in particular acyl bromides or chlorides, selectively to aldehydes. Examples of suitable starting materials are benzoyl chloride, salicyl chloride, 1- and 2-naphthoyl chloride, nicotinoyl and isonicotinoyl chloride, picolinoyl chloride, 2-furoyl chloride, thiophene- and pyrrole-2-carbonyl chloride and the corresponding acyl bromides. The stated radicals may also carry substituents which are inert under the reaction conditions, for example halogen, alkyl, alkoxy, hydroxyl, nitrile, ester, acid or amino groups.

The novel process can also be used to reduce halides of dicarboxylic acids, although overhydrogenation or cyclization reactions may occur in some cases.

The reaction according to the invention can be carried out batchwise or continuously under atmospheric, superatmospheric or reduced pressure by a conventional technique, for example in a stirred reactor or in a cylindrical reactor with circulation.

In an advantageous procedure, the halogen compound in solid, liquid or gaseous form, if necessary together with an inert gas, e.g. nitrogen, is fed to the reactor, which is heated at the reaction temperature. After the reaction, the reaction products leave the reactor as a rule in gaseous form together with the hydrogen halide formed. The products are isolated, for example, by condensing them either before or after removal of the hydrogen halide, depending on the boiling point, and if necessary purifying them, for example by distillation. The hydrohalic acids are advantageously removed by washing with water. The hydrohalic acids thus obtained are then neutralized and further used. If necessary, the hydrogen halide may also be neutralized directly by washing with an alkali.

The Examples which follow illustrate the invention and show the improvement achieved in comparison with the procedure described in German Laid-Open Application No. DOS 3,510,033 when the iron cocatalyst is used.

EXAMPLE 1a

Dehalogenation of 1,2-dichloropropane

In a 2 l stirred flask, 900 g of industrial white oil, 100 g of active carbon and 5 g of iron oxide (Fe$_2$O$_3$) were mixed and heated to a reacton temperature of 350° C. About 57 g (0.5 mole)/hour of 1,2-dichloropropane were fed in, with simultaneous passage of about 3 l/hour of nitrogen under the surface of the stirred reaction mixture. The gaseous reacted mixture was first condensed at from −10° to 0° C. in order to separate unconverted 1,2-dichloropropane and low boiling components from the oil. Thereafter, the gas stream was passed through a bubble tray column containing water in order to absorb the hydrogen chloride formed, and an aqueous hydrochloric acid was obtained in this manner. The exit gas, mainly propene, leaving the bubble tray column was measured by means of a gas meter and investigated by gas chromatography. The hydrochloric acid obtained was determined by titration. The activity of this reducing system, i.e. the conversion of 1,2-dichloropropane, decreased substantially only after an experimental time of 40 hours.

In an experimental time of 46 hours, a total of 2,610 g (23.1 moles) of 1,2-dichloropropane was passed in, 441 g (3.9 moles) of which were recovered as the unconverted compound. 738 g (17.5 moles) of propene and 1,345 g (36.9 moles) of hydrogen chloride were produced. Over the entire experimental time, this corresponds to a mean conversion of 83.1%, the propene selectivity being 91.1%.

EXAMPLE 1b

Dehalogenation of 1,2-dichloropropane (Comparative Example)

900 g of industrial white oil were mixed with 100 g of active carbon and heated to a reaction temperature of 350° C. The further procedure was described in Example 1a. However, the activity of this reducing system (without the presence of the iron cocatalyst) decreased sharply after only a relatively short experimental time. Whereas 14.7 g (0.35 mole)/hour of propene were initially produced, this value was only 5.0 g (0.12 mole) after 6 hours. Over the entire experimental time of 8 hours, only 75 g (1.8 moles) of propene could be prepared by this procedure.

EXAMPLE 2

Dehalogenation of 1,2-dichloropropane

The dehalogenation of 1,2-dichloropropane was carried out as described in Example 1a, except that, instead of 5 g of iron oxide, 3.9 g of iron sulfide (FeS) were used as the cocatalyst. In an experimental time of 44 hours, a total of 2,520 g (22.3 moles) of 1,2-dichloropropane was passed in, 496 g (4.4 moles) of which were unconverted. 676 g (16.1 moles) of propene and 1,244 g (34.1 moles) of hydrogen chloride were produced. Over the entire experimental time, this corresponds to a mean conversion of 80.3%, the propene selectivity being 89.9%.

EXAMPLE 3a

Dehalogenation of 1,2-dichloropropane

The procedure described in Example 1a was followed, except that the reaction temperature was only 300° C. In addition to 12.4 g (0.11 mole)/hour of unconverted 1,2-dichloropropane, 14.3 g (0.34 mole)/hour of propene and 27.0 g (0.74 mole)/hour of hydrogen chloride were obtained. This corresponds to a conversion of 78.2% and a propene selectivity of 87.2%.

EXAMPLE 3b

Dehalogenation of 1,2-dichloropropane (Comparative Example)

The procedure described in Example 3a was followed, except that no iron oxide was added to the reaction mixture.

In addition to 37 g (0.33 mole)/hour of unconverted 1,2-dichloropropane, 6.4 g (0.15 mole)/hour of propene were obtained. This corresponds to a conversion of only 35.1% and a propene selectivity of 88.2%.

EXAMPLE 4a

Dehalogenation of bromobenzene

In the apparatus described in Example 1a, 900 g of industrial white oil, 100 g of active carbon and 5 g of iron oxide ($Fe_2O_3$) were initially taken and heated to a reaction temperature of 350° C. About 79 g (0.5 mole)/hour of bromobenzene were fed in, with simultaneous passage of about 3 l/hour of nitrogen under the surface of the stirred reaction mixture. In an experimental time of four hours, 296 g of condensate were obtained, and were shown by gas chromatographic analysis to consist of 79.7% by weight (235.9 g) of bromobenzene and 12.5% by weight (37.0 g) of benzene. Accordingly, the conversion was 25.3% and the selectivity 93.1%.

EXAMPLE 4b

Dehalogenation of bromobenzene (Comparative Example)

The procedure described in Example 4a was followed, except that no iron oxide was added to the reaction mixture. In an experimental time of four hours, 331 g of condensate were obtained, and were shown by gas chromatographic analysis to consist of 91.2% by weight (301.9 g) of bromobenzene and 1.9% by weight (6.3 g) of benzene. Accordingly, the conversion was only 4.5% at a selectivity of 89.2%.

EXAMPLE 5a

Dehalogenation of 1-chloropropane

In the apparatus described in Example 1a, 900 g of industrial white oil, 100 g of active carbon and 5 g of iron oxide ($Fe_2O_3$) were initially taken and heated to a reaction temperature of 350° C. About 39 g (0.5 mole)/hour of 1-chloropropane were fed in, with simultaneous passage of from 1 to 2 l/hour of nitrogen under the surface of the stirred reaction mixture. The further procedure was as described in Example 1a. About 21 g (0.27 mole)/hour of unconverted 1-chloropropane were recovered and 2.9 g (0.07 mole)/hour of propene and 6.2 g (0.14 mole)/hour of propane were produced. This corresponds to a conversion of 46.0% and a propane selectivity of 60.9%.

EXAMPLE 5b

Dehalogenation of 1-chloropropane (Comparative Example)

The procedure described in Example 5a was followed, except that no iron oxide was added to the reaction mixture. About 33 g (0.42 mole)/hour of unconverted 1-chloropropane were recovered and 1.7 g (0.04 mole)/hour of propene and 1.3 g (0.03 mole)/hour of propane were produced. This corresponds to a conversion of 16.0% and a propane selectivity of 37.5%.

EXAMPLE 6a

Dehalogenation of 1,2-dichlorobenzene

About 15 g (0.1 mole)/hour of 1,2-dichlorobenzene and about 26 g (0.2 mole)/hour of tetralin were vaporized beforehand at 275° C. and fed, together with about 2 l/hour of nitrogen, to a fixed-bed reactor which was heated at 400° C. and filled with 100 g of a Supersorbon ® catalyst laden with 7.2% by weight of $Fe_2O_3$. The gaseous reaction products were first condensed at −10° C. and the gas stream then passed through a bubble tray column containing water in order to remove the hydrogen chloride formed. Titration of the hydrochloric acid formed showed that 5.5 g (0.15 mole)/hour of hydrogen chloride were produced. Accordingly, 75% of the chlorine bound in the 1,2-dichlorobenzene were removed by reduction. The condensate was shown to contain benzene and chlorobenzene as reaction products.

EXAMPLE 6b

Dehalogenation of 1,2-dichlorobenzene (Comparative Example)

The procedure described in Example 6a was followed, except that Supersorbon ® without added metal was used as the catalyst. Titration of the hydrochloric acid formed showed that 4.0 g (0.11 mole)/hour of hydrogen chloride were produced. Accordingly, only 55% of the chlorine bound in the 1,2-dichlorobenzene were removed by reduction.

We claim:

1. A process for the reductive dehalogenation of an organic halogen compound in which one or more halogen atoms selected from the group containing of iodine, bromine and chlorine are covalently bonded to the carbon, which process comprises:
    reacting said organic halogen compound with a hydrocarbon in the presence of carbon at a temperature of from 100° to 450° C. for dehalogenation with formation of a hydrogen halide, and carrying out the dehalogenation in the presence of iron powder or an iron compound as a cocatalyst.

2. A process as claimed in claim 1, wherein the hydrocarbon used is a high boiling mineral oil whose boiling point is higher than the reaction temperature.

3. A process as claimed in claim 1, wherein the hydrocarbon used is a vacuum residue, heavy fuel oil or industrial white oil.

4. A process as claimed in claim 1, wherein the iron compound used is iron(III) oxide, iron(II) sulfide or iron(II) disulfide.

5. A process as claimed in claim 1, wherein from 1 to 50% by weight of carbon and from 0.1 to 10% by weight of the iron compound are present in the reaction mixture.

6. A process as claimed in claim 1, wherein a low boiling hydrocarbon or a mixture of such hydrocarbons, such as light fuel oil, gasoline, naphtha or a liquefied petroleum gas, is used, and the reaction is carried out either under superatmospheric pressure in the liquid phase or under atmospheric pressure in the gas phase.

7. A process as claimed in claim 1, wherein a straight-chain, branched or cyclic monohaloalkane is reacted.

8. A process as claimed in claim 1, wherein an olefinically unsaturated monohalogen compound is reacted.

9. A process as claimed in claim 1, wherein a vicinal di- or polyhaloalkane or -cycloalkane is reacted.

10. A process as claimed in claim 1, wherein an aromatic halogen compound is reacted.

11. A process as claimed in claim 1, wherein an aromatic or heteroaromatic acyl halide is reacted.

12. A process as claimed in claim 1, wherein 1,2-dichloropropane is reacted.

13. A process as claimed in claim 1, wherein the reaction temperature is from 200° to 400° C.

14. A process as claimed in claim 1, wherein the reaction temperature is from 250° to 350° C.

* * * * *